United States Patent
Napoli et al.

(10) Patent No.: US 8,144,964 B1
(45) Date of Patent: Mar. 27, 2012

(54) IMAGE FEATURE ANALYSIS

(75) Inventors: Joshua Napoli, Arlington, MA (US); Sandy Stutsman, Watertown, MA (US)

(73) Assignee: Ellis Amalgamated LLC, Arlington, MA (US)

( * ) Notice: Subject to any disclaimer, the term of this patent is extended or adjusted under 35 U.S.C. 154(b) by 421 days.

(21) Appl. No.: 12/475,790

(22) Filed: Jun. 1, 2009

Related U.S. Application Data

(60) Provisional application No. 61/057,552, filed on May 30, 2008.

(51) Int. Cl.
*G06K 9/00* (2006.01)
*A61B 8/00* (2006.01)

(52) U.S. Cl. .......................... 382/131; 382/154; 600/440

(58) Field of Classification Search .......... 382/128–144, 382/154, 173; 606/27, 32–40; 600/437, 600/440
See application file for complete search history.

(56) References Cited

U.S. PATENT DOCUMENTS

| | | | | |
|---|---|---|---|---|
| 5,628,321 A | * | 5/1997 | Scheib et al. | 600/453 |
| 7,871,406 B2 | * | 1/2011 | Nields et al. | 606/27 |
| 2004/0054281 A1 | * | 3/2004 | Adam et al. | 600/437 |
| 2005/0163358 A1 | * | 7/2005 | Moeller | 382/128 |
| 2005/0169507 A1 | * | 8/2005 | Kreeger et al. | 382/128 |
| 2005/0285858 A1 | * | 12/2005 | Yang et al. | 345/420 |
| 2008/0218743 A1 | * | 9/2008 | Stetten et al. | 356/73 |
| 2009/0076388 A1 | * | 3/2009 | Napoli et al. | 600/437 |

* cited by examiner

*Primary Examiner* — Hoa Pham
(74) *Attorney, Agent, or Firm* — Cantor Colburn LLP

(57) ABSTRACT

A method for localizing hard objects in soft tissue utilizing a computer based system includes receiving ultrasound data from an ultrasound scanner and converting on the computer based system the ultrasound data into a reflectivity image. The method also includes selecting voxels from the reflectivity image that exceed an adaptive threshold, locating disjointed voxel clusters formed by the selected voxels, and outputting to an external processor locations of the voxel clusters that form a desired shape to an external processor.

7 Claims, 7 Drawing Sheets

```
1.   /* This is an OpenGL Shading Language source listing that implements a
2.      stream kernel. The kernel compares a voxel of the source image with the
3.      (approximate) median value of the portion of the beam that extends from
4.      the voxel position to the end of the beam. If the voxel intensity
5.      exceeds a given ratio, a positive value is returned. */
6.
7.   // Return a scalar value from the "main" function.
8.   void return_scalar( float value ) { gl_FragColor = vec4( value ); }
9.
10.  /* Compute a histogram of the intensity levels for the voxels of the
11.     beam that covers the given position, for the portion of the beam that
12.     extends from the point. The histogram is computed using four bins,
13.     separated by the three given bin threshold levels. */
14.  vec4 histogram_4bins
15.                    ( vec3 position, vec3 bin, sampler3D tex, vec3 step )
16.  {
17.    ivec4 histogram = ivec4(0);
18.    for(; position.x < 1.; position.x += step.x)
19.    {
20.      float intensity = abs( texture3D( tex, position ).r );
21.      if     ( intensity < bin.x ) histogram.x += 1;
22.      else if( intensity < bin.y ) histogram.y += 1;
23.      else if( intensity < bin.z ) histogram.z += 1;
24.      else                         histogram.w += 1;
25.    )
26.    return histogram;
27.  }
28.
29.  /* Return a positive value when the intensity level exceeds the median
30.     intensity by the given ratio. */
31.  float compare_median_4bins
32.                    ( float intensity, vec4 histogram, float ratio )
33.  {
34.    if( histogram.x > histogram.y + histogram.z + histogram.w )
35.      return intensity - ratio*bin.x;
36.    else if( histogram.x + histogram.y > histogram.z + histogram.w )
37.      return intensity - ratio*bin.y;
38.    else
39.      return intensity - ratio*bin.z;
40.  }
41.
42.  /* Return a positive value when the intensity level of the given image
43.     at the given position exceeds the median intensity by the given ratio.
44.     The median intensity is estimated using a 4-bin histogram with given bin
45.     thresholds. The "uniform" and "varying" variables are effectively
46.     function arguments. */
47.  uniform sampler3D image;    // source data array
48.  uniform vec3      step;     // source voxel step = 1 / array dimensions
49.  uniform float     ratio;    // min ratio of seed to median intensity
50.  uniform vec3      bin;      // intensities that separate histogram bins
51.  varying vec3      voxel;    // position of the voxel
52.  void main( void )
53.  {
54.    return_scalar
55.       ( compare_median_4bins
56.          ( abs(texture3D( image, voxel ).r ) // intensity of the image
57.          , histogram_4bins( position, bin, image, step )
58.          , ratio ) );
59.  }
```

Fig. 3

```
1.   /* This is an OpenGL Shading Language source listing that implements a
2.   stream kernel. The kernel maps a voxel with positive value to a
3.   three-vector whose value gives the coordinate within the volume. Non-
4.   positive voxel values are discarded (no output is generated). Applying
5.   this kernel to a threshold image creates a set-label image. */
6.
7.   // Return a vector value from the "main" function.
8.   void return_vec3( vec3 value ) { gl_FragColor = vec4( value, 1. ); }
9.
10.  /* When the intensity level of the given image at the given voxel is
11.  positive, return a vector giving the voxel position. Otherwise the
12.  fragment is discarded. The "uniform" and "varying" variables are
13.  effectively function arguments. */
14.  uniform sampler3D image;  // source data array
15.  varying vec3 voxel;       // position of the voxel
16.  void main(void)
17.  {
18.    if( texture3D( image, voxel ).r > 0. )
19.    {
20.      return_vec3( voxel );
21.    }
22.    else
23.    {
24.      discard;
25.    }
26.  }
```

Fig. 5

```
1.   /* This is an OpenGL Shading Language source listing that implements a
2.      stream kernel. The kernel defines an image mapping whose fixed point
3.      gives a unique label to each connected cluster. */
4.
5.   // Return whether a is less than b (in lexicographic ordering).
6.   bool compare( vec3 a, vec3 b )
7.   {
8.     if( a.x < b.x ) return true;
9.     else if( a.x == b.x )
10.      if( a.y < b.y ) return true;
11.      else if( a.y == b.y && a.z < b.z ) return true;
12.    return false;
13.  }
14.
15.  // Return the maximum value of seven 3-vectors.
16.  vec3 max7( vec3 a, vec3 b, vec3 c, vec3 d, vec3 e, vec3 f, vec3 g )
17.  {
18.    vec3 s10 = a;
19.    if( compare( a, b ) ) s10 = b;
20.    vec3 s11 = c;
21.    if( compare( c, d ) ) s11 = d;
22.    vec3 s12 = e;
23.    if( compare( e, f ) ) s12 = f;
24.    vec3 s20 = s10;
25.    if( compare( s10, s11 ) ) s20 = s11;
26.    vec3 s21 = s12;
27.    if( compare( s12, g ) ) s21 = g;
28.    vec3 s3 = s20;
29.    if( compare( s20, s21 ) ) s3 = s21;
30.    return s3;
31.  }
32.
33.  // Return a vector value from the "main" function.
34.  void return_vec3( vec3 value ) { gl_FragColor = vec4( value, 1. ); }
35.
36.  /* For non-discarded (nonzero) voxels, return the maximum adjacent set
37.     identifier. The "uniform" and "varying" variables are effectively
38.     function arguments. */
39.  uniform sampler3D image;  // source data array
40.  uniform vec3 step;        // source voxel step = 1 / array dimensions
41.  varying vec3 voxel;       // position of the voxel
42.  void main( void )
43.  {
44.    vec3 x = texture3D( image, voxel );
45.    if( x != vec3( 0. ) )
46.    {
47.       parent = max7
48.         ( x
49.         , texture3D( image, parent + step * vec3(-1., 0., 0.) )
50.         , texture3D( image, parent + step * vec3( 1., 0., 0.) )
51.         , texture3D( image, parent + step * vec3( 0.,-1., 0.) )
52.         , texture3D( image, parent + step * vec3( 0., 1., 0.) )
53.         , texture3D( image, parent + step * vec3( 0., 0.,-1.) )
54.         , texture3D( image, parent + step * vec3( 0., 0., 1.) ) ) );
55.      if( parent == x ) discard;
56.      else return_vec3( parent );
57.    }
58.    else discard;
59.  }
```

Fig. 6

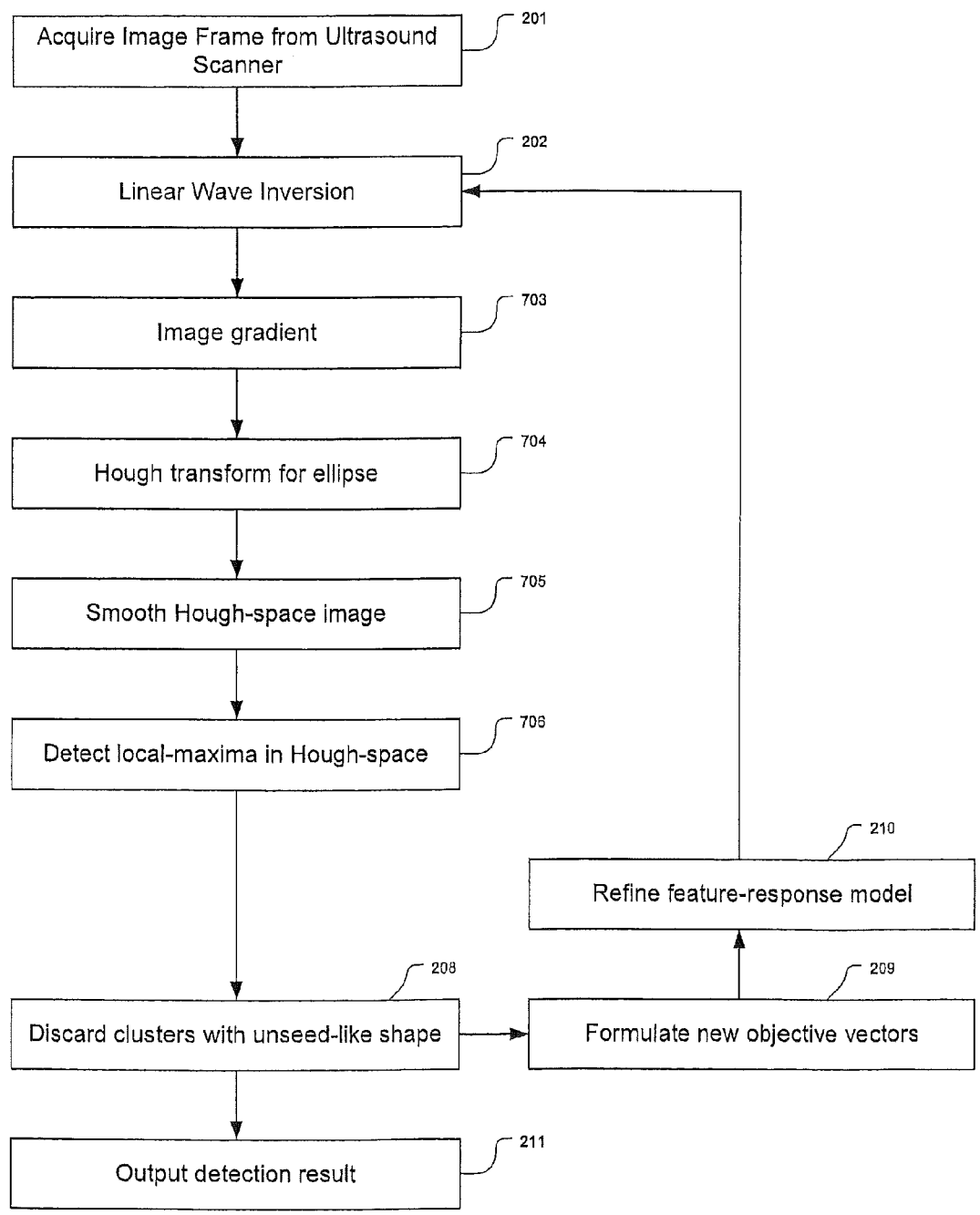

IMAGE FEATURE ANALYSIS

PRIORITY CLAIM

This application claims priority under 35 U.S.C. §119(e) to U.S. Provisional Patent Application Ser. No. 61/057,552, filed May 30, 2008, entitled Image Feature Analysis, and which is hereby incorporated by reference in its entirety.

BACKGROUND

The present invention relates to image analysis, particularly to ultrasound imaging of hard regions within biological tissue.

It is common to analyze imagery, such as ultrasound, computerized tomography, and photographic imagery, for the presence and location of various features. Typical applications of these so-called computer vision techniques are in the medical, military, and inspection fields.

As mentioned above, medical fields greatly really on imaging for the treatment and diagnosis of medical conditions. One example is in the context of medical ultrasound for prostate cancer treatment using permanent seed implant brachytherapy. Of course, imaging could be utilized in any other field as well and the teachings herein are not limited to the brachytherapy field.

As is well known, brachytherapy involves the precise placement of 50-100 tiny (e.g. 0.8 mm×4.5 mm) titanium "seeds" with a radioactive core. The seeds are placed with the assistance of real-time trans-rectal ultrasound (TRUS) imagery, such as that provided by a B-K Medical ProFocus TRUS. The clinicians also typically rely on computer software to assist in the planning and placement of the seeds. The software can compute the expected or desired radiation at various points in the body as a function of seed location. Clinicians seek, for example, to provide a certain prescribed radiation dose at the prostate while minimizing the dose to surrounding tissue, such as the urethra and rectum.

However, current ultrasound technologies make it difficult for the clinician or the planning software to identify and localize the positions of the seeds within the body for a variety of well-known reasons.

One system that incorporates these image analysis operations is the TRUS itself, as embedded software. Another system incorporating these image analysis operations is a computing device in communication with the TRUS.

Terms such as "stream processor" and "stream kernel" are terms pertaining to the field of computer science, particularly in the context of programming parallel processing systems such as general-purpose graphics processing units (GPG-PUs). An example GPGPU is the NVIDIA GeForce 9800 GTX (Santa Clara, Calif.).

SUMMARY

According to one embodiment of the present invention, a method for localizing hard objects in soft tissue utilizing a computer based system is disclosed. The method of this embodiment includes receiving ultrasound data from an ultrasound scanner; converting on the computer based system the ultrasound data into a reflectivity image; selecting voxels from the reflectivity image that exceed an adaptive threshold; locating disjointed voxel clusters formed by the selected voxels; and outputting to an external processor locations of the voxel clusters that form a desired shape to an external processor.

Another embodiment of the present invention is directed to a computer implemented method of refining a reflectivity model used to locate hard objects in soft tissue. The method of this embodiment includes receiving at a computer an ultrasound data from an ultrasound scanner; converting on the computer the ultrasound data into a reflectivity image, the conversion being based on an original reflectivity model; determining with high-confidence a location of a hard object; revising the reflectivity model based on RF data associated with the hard object.

In yet another embodiment, a method for localizing hard objects in soft tissue utilizing a computer based system is disclosed. The method of this embodiment includes receiving ultrasound data from an ultrasound scanner; converting on the computer based system the ultrasound data into a reflectivity image; generating a gradient of the reflectivity image; applying a Hough transform to the reflectivity image to the reflectivity gradient image to generate a Hough-space image containing descriptions of shapes of voxels in the Hough-space image;
increasing a voxel intensity for voxels having a desired shape; selecting particular voxels; and outputting to an external processor locations of the voxel clusters that form a desired shape to an external processor.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 3 is a source listing for an OpenGL Shading Language implementation of a stream kernel that can be used in the computation of a threshold volume from an RF image volume;

FIG. 4, FIG. 5 and FIG. 6 illustrate a process for labeling disjoint clusters of connected voxels. FIG. 4 is a flowchart which describes a method of labeling disjointed clusters;

FIG. 5 is a source listing for an OpenGL Shading Language implementation of a typical stream kernel for the initialization process;

FIG. 6 is a source listing for an OpenGL Shading Language implementation of a typical kernel of the parallel region-growing mapping step; and FIG. 7 is a flow chart listing the processing stages for localizing seeds using a Hough transform.

DETAILED DESCRIPTION

Embodiments of the present invention may be described in the context of medical ultrasound, in which an ultrasound system is capable of providing B-mode and/or (raw) "RF data" to a computer or other device that executes one or more image analysis algorithms disclosed herein. Of course, the teachings herein could be applied in other fields where B-mode or RF are received. The following discussion will focus on the case where seeds have been implanted in a prostate.

One method to identify seeds is to perform various thresholding operations as a function of reflectivity or reflection intensity. Titanium seeds have much higher acoustic impedance than prostate tissue and therefore produce a very strong reflection. As is known in the art, ultrasound images may be represented as a collection of voxels. A voxel is a volume element, representing a value on a regular grid in three dimensional space. Voxels with very high reflection intensity are likely to contain a seed.

Reflection intensity can be computed by low-pass filtering the raw reflection signal. Reflectivity can be computed by linear wave inversion. Linear wave inversion is described in U.S. patent application Ser. No. 12/212,919, entitled ULTRASOUND LINEAR WAVE INVERSION AND DETECTION OF HARD OBJECTS, and is incorporated herein by reference.

Figure 1:
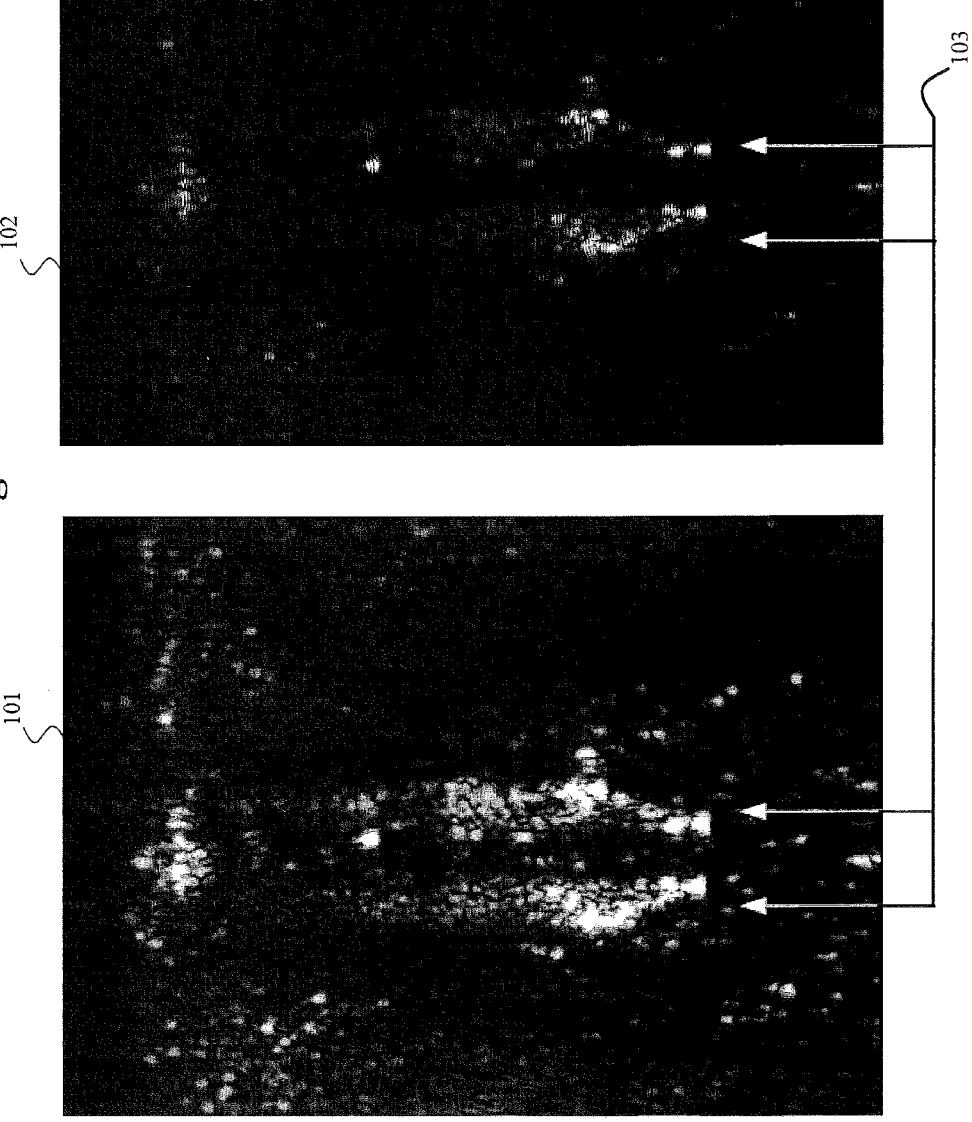
FIG. 1 is an illustration of a B-mode image and an RF image of two tilted seeds.
Figure 2:
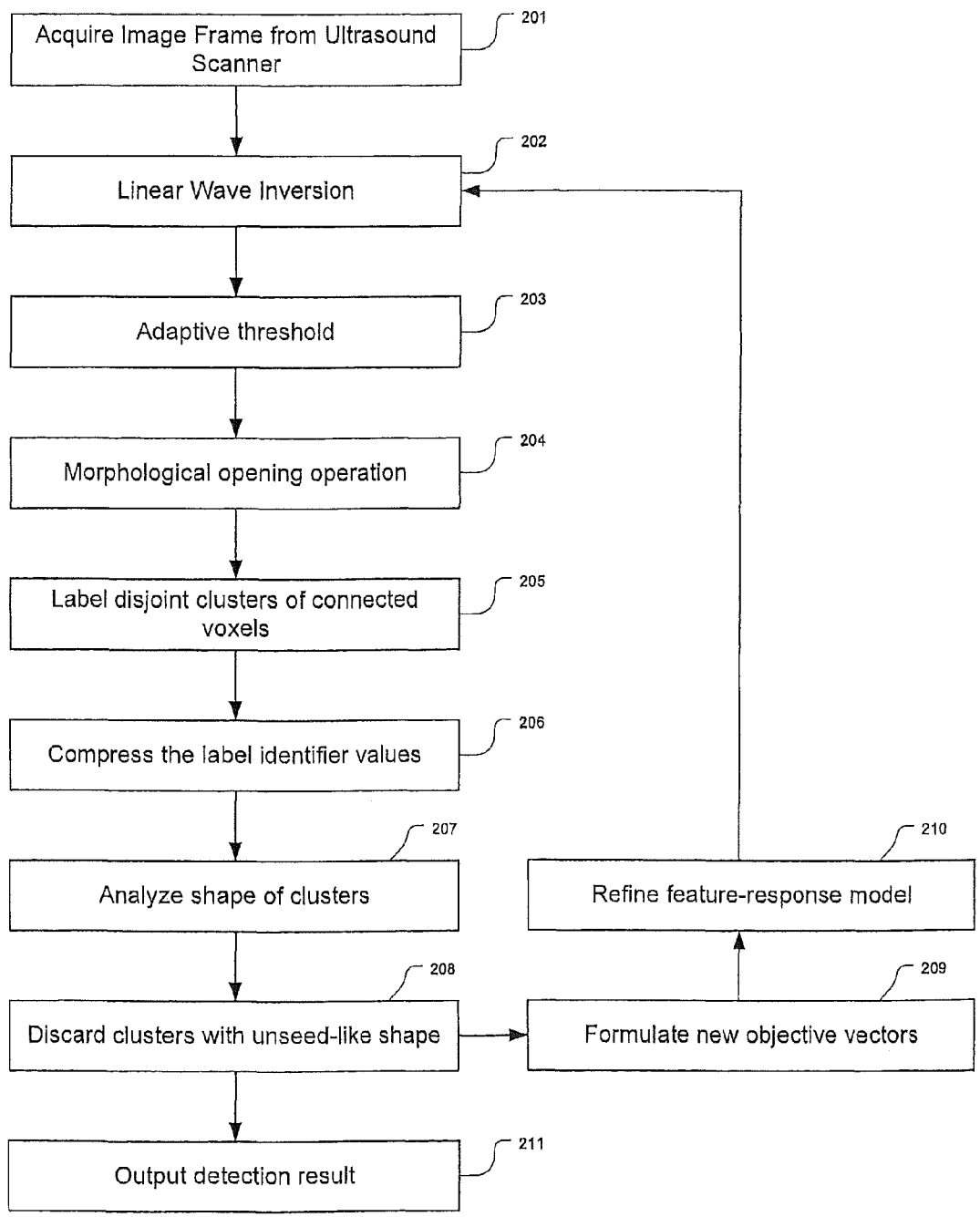
FIG. 2 is a flow chart listing the processing stages for localizing seeds using thresholding.

A process for localizing seeds using thresholding according to an embodiment of the present invention is illustrated in summary in FIG. 2.

An image frame containing RF (raw) ultrasound data (102) is acquired from an ultrasound scanner at a block 201. An example of such an ultrasound scanner may include the B-K Medical Pro Focus 2202 with the Type 8848 transducer. It is to be understood that the image frame may either refer to a 2-D or a 3-D image, depending on the type of ultrasound scanner and probe in use and also depending on whether a system is in place to accumulate the 2-D image frames from a 2-D probe into a 3-D composite image frame. Optionally, a reflectivity image is derived from the RF ultrasound image. In a reflectivity image, the value of each voxel gives its tendency to scatter acoustic energy back to the transducer. One way to convert from an RF ultrasound image to a reflectivity image is linear wave inversion as indicated at optional block 202. In one embodiment, an adaptive threshold is applied at a block 203 to select voxels with high reflectivity.

Next, a morphological opening operation is applied at a block 204. Disjoint clusters of connected voxels are then detected at a block 205 and are given cluster label identifier values. The cluster label identifier values are compressed at a block 206. The moments of each cluster are then calculated at a block 207. Based on the moment calculation, clusters that do not have the shape of a seed are rejected at a block 208.

At this point, a detection result is output at a block 211. The result may be output, a dosimetry engine, for example.

The mapping from the RF image to the reflectivity image is a global operation, meaning that many parts of the RF image affect the value of each voxel of the reflectivity image. Practical means for evaluating this mapping generally involve a reflectivity model that characterizes the signal conduction through the imaged medium. For example, in linear wave inversion (block 202), the reflectivity model consists of a reflectivity basis. The parameters of the model cannot generally be directly measured. One way to determine the model is to solve the model parameters that best fit a set of training vectors. Each training vector relates a feature with known reflectivity to its characteristic in the RF image.

Optionally, the detected seeds may also used to formulate new training vectors at a block 209. The new training vectors are used to refine the feature-response model at a block 210 to improve the linear wave inversion process of block 202. The improved linear wave inversion process can be applied to the current ultrasound frame, future frames or even retroactively applied to stored ultrasound frames.

Some areas of the prostate may be "shadowed" due to the presence of artifacts in the prostate. Shadowed areas can be caused by hemorrhaging in the prostate or air-based contrast agent in the urethra. The reflection intensity is reduced at points along the beam farther from the transducer than the artifact. The adaptive threshold process of block 203 for identifying likely seed locations can overcome this artifact by comparing the voxel intensity with the median reflection intensity for the portion of the beam that extends beyond the voxel away from the transducer. Voxels that exceed the median or average reflection intensity by a given ratio are likely to contain a seed. The adaptive thresholding of block 203 maps the reflectivity image to a threshold image.

The source listing of FIG. 3 provides an example of one way to implement this process. The technique can be implemented on a stream processor using a filter kernel, such as the one described by the source listing shown in FIG. 3. For each source voxel, the stream processor executes the filter kernel (FIG. 3). The filter kernel (FIG. 3) evaluates the threshold condition and outputs the result given by the sign of its return value. The return value for each source voxel defines a threshold image, which is formed by the stream processor.

The threshold image identifies a set of voxels that potentially intersect with a seed. Typically, multiple seeds are imaged within a single volume and therefore another step is required to identify discrete seed positions and their supporting voxels. In loose seed implants, it is common for seeds to "wake" behind the needle, following the needle for some distance as it is withdrawn from the prostate. This commonly results in two or more seeds nearly touching end-to-end. Due to the "wake" phenomenon with loose seeds, two or more seeds may be nearly touching. To avoid combining nearby seeds into a single connected cluster, the morphological opening operation of block 204 may be performed on the threshold image. The operation is preferably performed using a spherical structuring element whose diameter matches the diameter of the cross section of the seed (typically 0.8 mm). The morphological opening operation is defined as an erosion operation followed by a dilation operation, both using the given structuring element. Optionally, a grayscale opening operation may be performed on the reflectivity image instead of on the threshold image.

Figure 4:
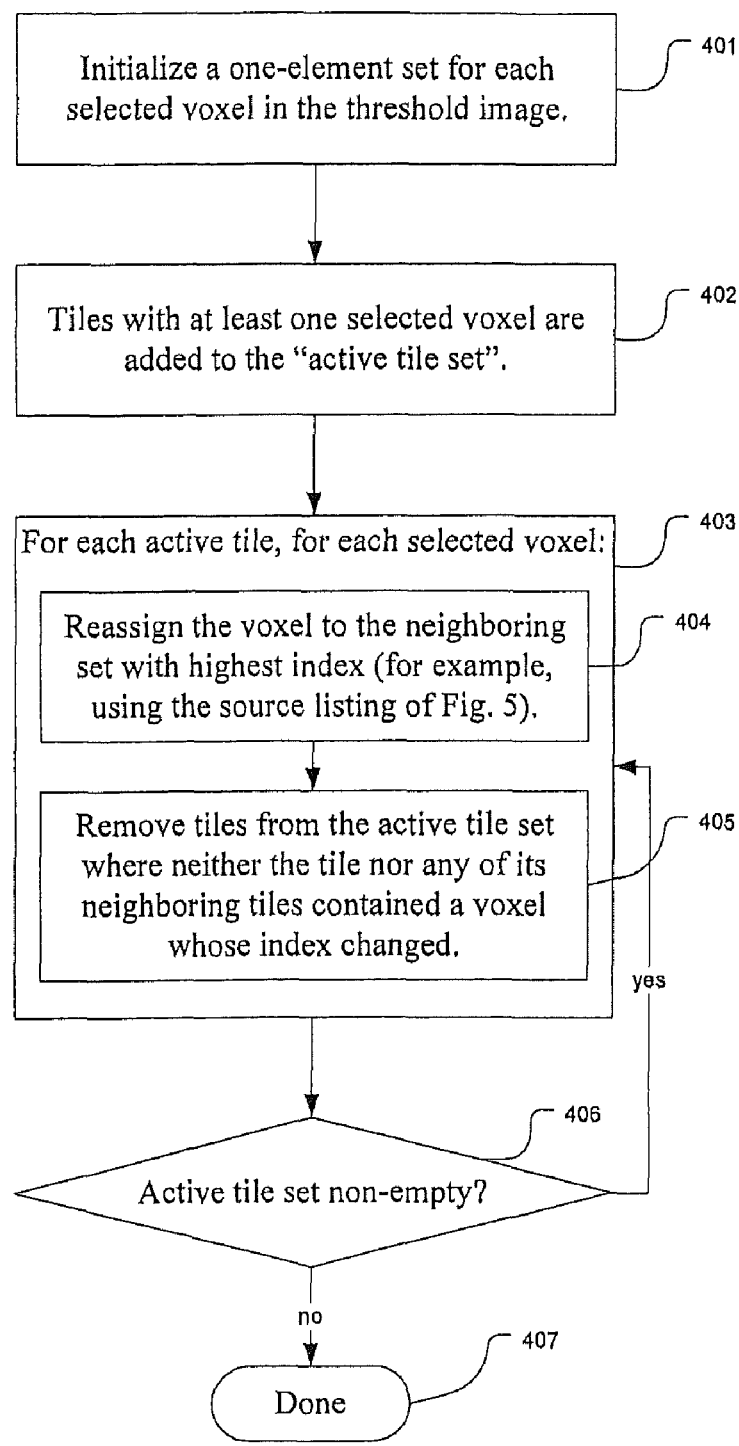

FIGS. 4, 5 and 6 illustrate the labeling operation in block 205 of FIG. 2. The disjoint clusters of connected seeds can be efficiently labeled using a union-find algorithm. Voxels selected by the adaptive threshold are assigned into disjoint sets. The algorithm iterates over the voxels, merging sets that are found to contain neighboring voxels.

On a stream processor, clusters can be identified as the fixed point of a parallel region-growing image mapping operation. For a stream processor implementation, the image space is preferably partitioned into one or more tiles, such that events of the algorithms operator can be counted in each tile.

To begin with and referring now to FIG. 4, a cluster label image is initialized at a block 401 with a singleton cluster for each selected voxel of the threshold image. Tiles with at least one selected voxel are added at a block 402 to the "active tile set". Next, the fixed point of a transformation on the cluster label image is searched for at a block 403. The transformation is applied recursively until the cluster label image no longer changes at determined at a block 406. To implement each transformation, each active tile is processed. For each active tile, for each selected voxel, the voxel is reassigned to the neighboring set with highest index at a block 404. The source listing of FIG. 5 provides an example implementation of what may be performed at block 404.

Tiles are removed from the active tile set in the event that a tile and all of its neighbors remained unchanged at a block 405. The processing of active tiles is repeated until the active tile set is empty as determined at a block 406. The fixed point has been reached when the active tile set is empty as determined at a block 407.

The labels stored in the cluster label image may be unwieldy for the remaining processing stages. In the example implementation that is detailed in the previous paragraphs, the index for each cluster stores an x,y,z coordinate. For convenience and efficiency, each label can be mapped to a small integer as discussed above with respect to block 206 of FIG. 2. This may be accomplished by iterating over the cluster label image and populating a mapping data structure that identifies each cluster label with a sequence number. A compressed cluster label image is then formed by replacing each cluster label with the corresponding sequence number.

Referring again to FIG. 2, calcifications in the prostate can produce reflection intensities that match seed reflection intensities. Calcifications are a problem for seed detection because they are often coincident with prostate cancer. To reliably distinguish between voxels that contain seeds and voxels that contain calcium deposits, the shape of the hard feature must be taken into account. Seeds are engineered with tight tolerances on their shape, while natural calcifications are irregularly shaped. It is unlikely that a calcification would happen to have the exact shape as a seed. To analyze the shape of each cluster, its moments of inertia may be calculated at a block 207. Preferably, this includes the total mass, the center of mass, and inertia tensor (second moments). The singular value decomposition of the inertia tensor gives the magnitude of the major and minor axes of an ellipse that approximates the cluster. If the major axis is not near the expected length of the seed (typically 4.5 mm) or the minor axes are not near the expected diameter of the seed (typically 0.8 mm), then the cluster is rejected at a block 208 and assumed to represent a calcification.

The validated clusters may now be output at a block 211 for use by other parts of the software, such as a dosimetery engine. The brachytherapy seeds, with known size and density, can also be used to refine the reflectivity model of the mapping from the RF image to the reflectivity image. The reflectivity model can be refined at positions identified by high-confidence seed positions. The validated clusters can also be used to form new training vectors as indicated at a block 209 to improve the model at a block 210 used by the linear wave inversion step. A training vector consists of RF data from a neighborhood of the detected seed, preferably extending beyond the end of the seed's "tail". The RF image of the seed is skewed to bring the tilt of the seed level with the probe. The RF data of a training vector may be adjusted to place the seed into a regular orientation. For example, in preparing a training vector from a tilted seed, the RF data is skewed to place the seed into its regular orientation.

The convolution kernel can be refined using Linear Least Squares. A convolution matrix, A, is constructed using the tilt and depth offset of the training vectors. In the Mathematica listing below, the ConvolutionMatrix function forms the convolution matrix.

Iterators[array_,name_,lb_,ub_]:=Iterators[array,name,Array[lb&,ArrayDepth[array]],Array[ub&,ArrayDepth[array]]]
Iterators[array_,name_]:={name#,1,Dimensions[array][[#]]}&/@Range[ArrayDepth[array]]
Iterators[array_]:=Iterators[array,i]
ToSequence[list_]:=ReplacePart[list,0→Sequence];
IteratorSequence[array_,supportInterval_,x_]:=ToSequence[Iterators[array,i,Ceiling[x+Min[supportInterval]],Floor[x+Max[supportInterval]]]];
LinearKernel[s_]:=Piecewise[{{1-Abs[s],Abs[s]<1}}]/;NumberQ[s]
LinearKernel[s_List]:=Piecewise[{{Times@@(1-Abs[s]),Max[Abs[s]]<1}}]
SymmetricInterpolation[array_,kernel_,supportInterval_]:=Sum[Extract[array,IteratorVariables[array]] kernel[#-IteratorVariables[array]],Evaluate[IteratorSequence[array,supportInterval,#]]]&
TranslateWaveLinear[wave_,x_]:=Array[SymmetricInterpolation[wave,LinearKernel,Interval[-3/2,3/2]][[#-x]]&,Length[wave]]
SkewLinear[array_,rate_]:=Array[TranslateWaveLinear[array[[#]],(#-1)rate]&,Length[array]]
SeedFootprint[offset_,n_]:=SparseArray[{offset→1,offset+12→-1},{n}]/;offset+12≦n
SeedFootprint[offset_,n_]:=SparseArray[{offset→1},{n}]/;offset+12>n&&offset≦n
SeedFootprint[offset_,n_]:=SparseArray[{ },{n}]/;offset>n
Objective[n_,skew_,offset_]:=SkewLinear[Array[SeedFootprint[offset,n]&, 3],skew]
Seed[seed_,skew_]:=SkewLinear[Array[seed&,3],skew]
ConvolutionMatrix[kernelLength_,samples_,skew_]:=Array[Flatten[Objective[kernelLength,skew,#]]&,samples]
SolveFromExamples[convolutionMatrix_,objectiveVectors_]:=LeastSquares[Flatten[Array[convolutionMatrix&,Length[objectiveVectors]],1],Flatten[objectiveVectors,1]]

The convolution kernel that is optimal in the least squares sense is given by argmin (|Ax-y|; x), where A is the convolution matrix, x is the seed footprint and y is the objective vector. The convolution matrix is typically a sparse matrix. Objective vectors are typically approximately one thousand samples. With multiple objective vectors, the convolution matrices, seed footprints and objective vectors are concatenated. This is illustrated by the SolveFromExamples function in the source listing above.

A further refinement in the quality of the solved kernel can be made through a maximum a posteriori estimation of the kernel, subject to a prior distribution that characterizes the expected shape of the kernel.

The Hough Transform has proven to be effective in CT seed localization and in ultrasound needle localization. The "wake" phenomenon occasionally results in two seeds falling side-by-side. This presents a special difficulty. The relatively large lateral extent of the point spread function of typical ultrasound probes, side-by-side seeds can be blurred into one apparent body.

A Hough Transform can be used to overcome this difficulty by providing a more rich analysis of the shape of clusters. FIG. 7 gives an overview of the seed detection process using the Hough Transform. Image acquisition (201), linear wave inversion (202), shape selection (208) and model refinement (209 and 210) proceed in the same manner as seed localization with thresholding as described above. The Hough transform starts with the gradient of the reflectivity image at a block 703. The Hough transform is applied at a block 704 to the reflectivity gradient image to generate a Hough-space image. A Hough-space coordinate defines a particular ellipsoid. For example the Hough-space point (x, y, z, a, b, c, theta, phi) corresponds to the ellipsoid centered at (x, y, z), with axes (a,b,c) and orientation (theta, phi). Thus, each voxel in the Hough-space image corresponds to a particular set of ellipsoid parameters. In practice, the parameters a, b, c, theta and phi are highly quantized and stored in a single array dimension. Typically, a total of 256 sets of values are used.

The voxel intensity level is increased whenever a voxel in the reflectivity gradient image is compatible with the corresponding set of ellipsoid parameters. Since Hough-space is voxelized, a finite set of ellipsoid parameters are represented. A set of parameters that is rich in plausible seed ellipsoids is preferable. After the Hough-space image is computed at a block 704, it is smoothed at a block 705. Local maxima are detected in the smoothed Hough-space image at a block 706, and each maxima is taken to be a candidate seed. Just as with threshold-based seed detection, candidates are rejected whose ellipsoid parameters that are unlike actual seeds.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for localizing hard objects in soft tissue utilizing a computer based system, the method comprising:
   receiving ultrasound data from an ultrasound scanner;
   converting on the computer based system the ultrasound data into a reflectivity image;
   selecting voxels from the reflectivity image that exceed an adaptive threshold;
   locating disjointed voxel clusters formed by the selected voxels; and
   outputting to an external processor locations of the voxel clusters that form a desired shape to an external processor.

2. The method of claim 1, wherein the selected voxels form a threshold image that identifies a set of voxels which potentially intersect with a one of the hard objects.

3. The method of claim 2, wherein selecting includes comparing a voxel intensity with a median reflection intensity for a portion of a beam extending away from a transducer of the ultrasound scanner.

4. The method of claim 3, further comprising:
   performing a morphological opening operation of one or more clusters in the threshold image.

5. The method of claim 2, further comprising:
   labeling each voxel cluster.

6. The method of claim 5, wherein one or more of labels is mapped to a small integer.

7. The method of claim 1, further comprising:
   calculating moments of inertia for one or more of the clusters; and
   distinguishing between hard objects and calcification in the soft tissue based on the moments of inertia.

* * * * *

UNITED STATES PATENT AND TRADEMARK OFFICE
CERTIFICATE OF CORRECTION

| | | |
|---|---|---|
| PATENT NO. | : 8,144,964 B1 | Page 1 of 1 |
| APPLICATION NO. | : 12/475790 | |
| DATED | : March 27, 2012 | |
| INVENTOR(S) | : Joshua Napoli and Sandy Stutsman | |

It is certified that error appears in the above-identified patent and that said Letters Patent is hereby corrected as shown below:

Column 8, lines 21-22, cancel the text "to an external processor".

Signed and Sealed this
Third Day of July, 2012

David J. Kappos
*Director of the United States Patent and Trademark Office*